United States Patent [19]
Saylor

[11] Patent Number: 5,843,094
[45] Date of Patent: Dec. 1, 1998

[54] TICK REMOVING DEVICE

[76] Inventor: Pearl Saylor, deceased, late of Coldiron, Ky.

[21] Appl. No.: 881,593

[22] Filed: Jun. 24, 1997

[51] Int. Cl.[6] ................................................. A61B 17/50
[52] U.S. Cl. ............................................. 606/131; 606/1
[58] Field of Search ..................... 606/205–211, 131, 606/133, 1; 294/99.2; 254/18, 21, 25, 28

[56] References Cited

U.S. PATENT DOCUMENTS

| | | |
|---|---|---|
| 4,213,460 | 7/1980 | Weiner . |
| 4,938,764 | 7/1990 | Glaberson . |
| 5,078,729 | 1/1992 | Eichhorn . |
| 5,116,347 | 5/1992 | Butler . |
| 5,407,243 | 4/1995 | Riemann . |
| 5,447,511 | 9/1995 | Gadd . |

*Primary Examiner*—Glenn K. Dawson
*Attorney, Agent, or Firm*—Richard C. Litman

[57] ABSTRACT

A device is provided for removing ticks which are anchored in the skin of animals or humans. The tick removing device includes an elongated body and a tick engaging portion extending integrally from one end of the elongated body. The tick engaging portion includes a pair of legs which are flat and curved in a hook like manner towards the opposite end of the elongated body. The legs define a tick engaging slot suited for snug fitting around the neck portion of the tick. The tick engaging slot is sized such that it is of generally smaller dimensions than the body of a tick so as to permit removal of the tick.

6 Claims, 2 Drawing Sheets

TICK REMOVING DEVICE

BACKGROUND OF THE INVENTION

1. Field of the Invention

The present invention relates to devices for removing foreign objects from the skin, and more particularly to those devices suited for removing ticks from the skin of animals and humans.

2. Description of Related Art

Ticks have long been a problem for both animals and humans. Ticks will typically embed their heads into the host's skin and remain attached while feeding on the host's blood. As the tick feeds, its body becomes engorged with the host's blood. It is well known that ticks can carry a number of viruses and bacteria which may be transmitted to the host while the tick is feeding. Furthermore, the organisms transmitted by the tick can cause Lyme disease, Rocky Mountain Spotted Fever, Colorado tick fever, to name a few.

The tick uses a hollow snout which resembles the nose of a sawfish in order to suck the host's blood. When the tick removes its snout from the host, it automatically regurgitates a small portion of blood leaving it behind in the flesh of the host. In the case of Lyme disease, medical research has recently concluded that the responsible organism is only injected into the host during the regurgitation process. Furthermore, it is known that Lyme disease is most often contracted not because a host was bitten by a tick, but rather because the tick was improperly removed. Accordingly, it should be understood that many of the common methods used to remove ticks are improper, and in some cases can actually promote the spread of Lyme and other tick-borne diseases. Common methods of removing ticks include use of the fingers or tweezers, application of heat, chemical baths, and rotation of the tick in order to remove the snout.

Grabbing the tick with the fingers is undesirable because it squeezes the tick's posterior and can often result in injecting disease causing organisms into the host. When using this method, a person will usually employ his or her free hand to hold tissue for receiving the removed tick. As is often the case, the person loses the location of the wound and subsequently becomes unable to perform an examination or apply medication. This method can also pull out some of the host's hair, causing considerable pain and discomfort. Finally, direct contact with ticks is considered repulsive by many, and may even contribute to the spread of diseases found on the tick's surface.

Using tweezers is undesirable, as the hand holding them usually obstructs one's view of the invading organism during use, and considerable dexterity is required to place the two tiny gripping surfaces of the tweezers around the tick when the host has thick fur. Even then, the closing of the tweezer's jaws, especially if their opposing faces are flat or nearly so, will pinch the tick's posterior and inject the host with a portion of the blood meal while simultaneously pulling hair from the host. Also, using tweezers can lead to dropping the tick from the jaws as the implement's legs spring open when the tweezers are set down. Finally, if the second hand is required for disposal, subsequent difficulty may be encountered in relocating the wound for examination and application of medication.

Applying heat is undesirable because when the tick backs away from the host in an attempt to escape the burning or fumes, it may activate its regurgitation process and inject disease causing organisms into the host. This activity can often burn the host or the individual attempting to remove the tick. Furthermore, the application of too much heat can render the tick incapable of subsequent analysis by public health officials.

Applying chemicals can also cause the tick to regurgitate as it attempts to breathe clean air or escape the discomforts created by the chemicals. The host is also subject to certain discomfort, and the chemicals may irritate the wound, thus requiring subsequent cleaning.

Finally, rotating the tick in an attempt to dislodge it from the host is very likely to decapitate the tick. Thus, the snout remains buried in the host and is likely to irritate and possibly infect the host.

Many devices have been proposed for removing ticks, some of which are commercially available. However, most of these devices are fairly complex, and many fail to remove a wide variety of the tick species which may be encountered by humans and animals. For example, U.S. Pat. No. 4,213,640 issued on Jul. 22, 1980 to Weiner discloses tick removing forceps. The forceps include a pair of closable arms having cup-shaped gripping members affixed to the ends of the arms. The cup-shaped gripping members are adapted to close upon and grip the protruding portion of a tick. At least one of the gripping members is provided with an electrical thermal element or a chemical applicator affixed to its inner surface. When applied to a tick, the electrical thermal element causes it to release its bite on the host animal whereupon it can be easily removed by the forceps:

U.S. Pat. No. 4,938,764 issued on Jul. 3, 1990 to Glaberson discloses a tick remover including an elongated handle and a wire loop formed integrally with the handle. The wire loop also includes a contiguous opening which is large enough to receive the neck of the tick, but not large enough to receive the body. Thus, the contiguous opening may be fitted about the neck of the tick so that the head may be pulled from the skin.

U.S. Pat. No. 5,078,729 issued on Jan. 7, 1992 to Eichhorn discloses a tick removal tool. The tool includes a pair of interlocked pivotal clamping members. The clamping members have opposing, openable jaws which normally reside in the closed position. The clamping members are structured for enclosing the body of an embedded tick within a cavity formed between the closed jaws. One jaw includes a semi-circular notch centered with the cavity such that an aperture is formed when the jaws are closed. The aperture is sized for snugly fitting over the neck of the tick so as to hold and prevent severing of the neck. A compression spring is provided for generating the force necessary to maintain the clamping members in the closed position.

U.S. Pat. No. 5,116,347 issued on May 26, 1992 to Butler discloses a tick remover for people and animals. The device is in the form of a plier instrument whose jaws are uniquely designed for easy opening and accurate placement around a tick. The device includes a small gap which is formed when the jaws are closed around the tick. The jaws feature dull edges which include convex shaped cross sections along their length which enable secure grasping of the tick without severing its posterior from the head.

U.S. Pat. No. 5,407,243 issued on Apr. 18, 1995 to Riemann discloses a tick removing device. The device includes an elongated sleeve with a gripping device inserted therethrough. The gripping device includes a pair of flexible and spaced apart legs that are movable between open and closed positions via an actuator button disposed in the rear end of the sleeve. A pin mounted in the sleeve extends between the gripping legs to wedge them apart as the gripping device moves through the sleeve. The gripping legs are positioned about an attached tick while in the open position, and the actuator button is released in order to close the legs and grip the tick.

U.S. Pat. No. 5,447,511 issued on Sep. 5, 1995 to Gadd discloses a tick removal tool for removing anchored ticks from the skin of an animal or a human. The tool includes an elongated member having a longitudinal axis, a lateral axis, a forward edge, and a handle end. A tapered slot, which diverges towards and merges with the forward edge, is formed within the elongated member. The tool is manipulated such that the mouth parts and head of the tick are positioned and secured within the tapered slot.

None of the above inventions and patents, taken either singularly or in combination, is seen to describe the instant invention as claimed. Thus a tick removing device solving the aforementioned problems is desired.

SUMMARY OF THE INVENTION

Accordingly, it is a principal object of the invention provide a tick removing device for removing ticks from animals and humans.

It is another object of the invention to provide a tick removing device constructed of lightweight materials.

It is an object of the invention to provide improved elements and arrangements thereof in a tick removing device for the purposes described which is inexpensive, dependable and fully effective in accomplishing its intended purposes.

In accordance with the objects of the invention, a lightweight tick removing device is provided for removing ticks which are anchored in the skin of animals or humans. The tick removing device includes an elongated body and a tick engaging portion extending integrally from one end of the elongated body. The tick engaging portion includes a pair of legs, each of which terminate in a converging end. The legs are flat and curved in a hook-like manner toward the opposite end of the elongated body. Together, the legs define a tick engaging slot which is capable of being fitted around the neck portion of the tick. The tick engaging slot is also sized such that it is of generally smaller dimensions than the body of a tick so as to permit removal of the tick. A loop may be integrally formed from the end of the elongated body opposite the tick engaging portion in order to provide convenient storage and transportation. The tick removing device may be constructed of various lightweight materials such as aluminum or plastic in order to decrease cost and weight.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENT

Figure 1:
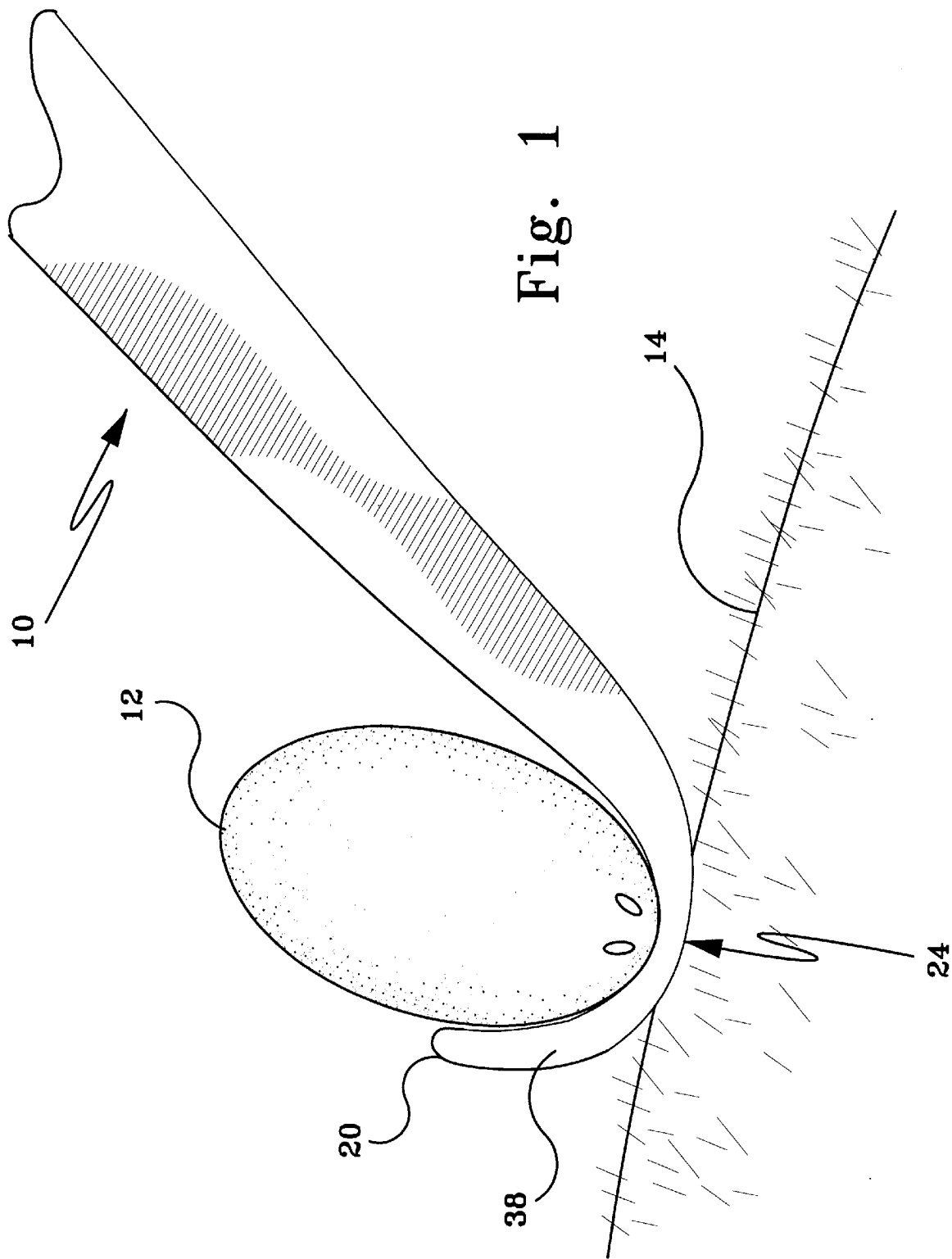
FIG. 1 is a greatly enlarged environmental, elevational and fragmented view of the tick engaging portion of a tick removing device in accordance with the present invention.
Figure 2:
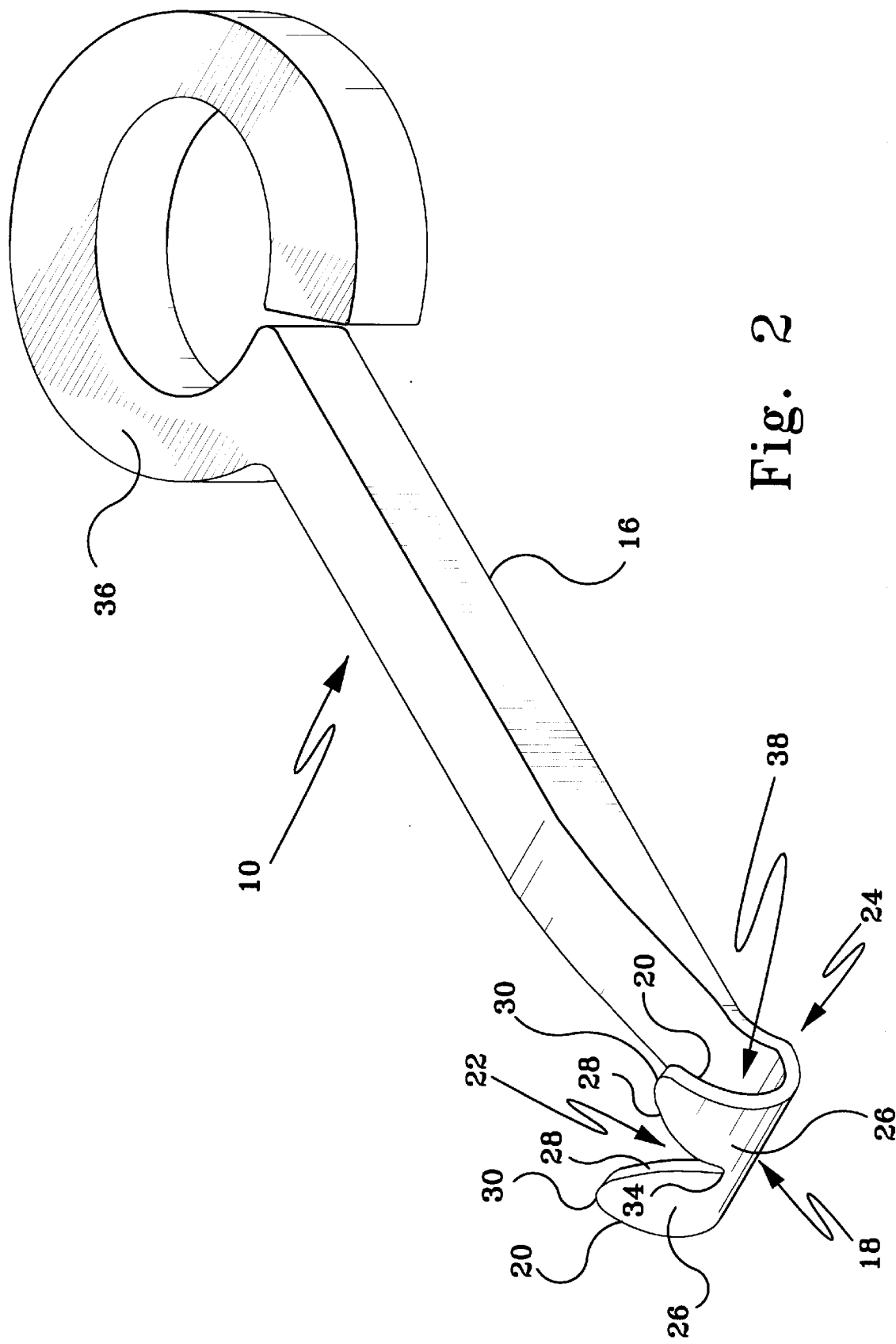
FIG. 2 is a perspective view of the tick removing device.

Referring to FIGS. 1 and 2 of the drawings, a tick removing device 10 is shown for removing ticks 12 which are anchored in the skin 14 of animals or humans. The tick removing device 10 includes an elongated body 16 and a tick engaging portion 18 which extends from one end of the elongated body 16. The tick engaging portion 18 includes a pair of legs 20 which are flat and terminate in a hook-like or a substantially U-shaped curvature 38 toward the opposite end of the elongated body 16. The substantially U-shaped curvature 38 circumscribes an angle greater than 90° and defines a pivotal surface 24 to serve as a fulcrum for levering the tick from the skin.

The configuration and spatial positioning of each of the legs 20 to one another define a tick engaging slot 22 capable of being fitted around the neck portion of the tick 12. Each of the legs 20 has a convergent end 26, which joins that portion of the tick engaging end 18 having pivotal surface 24. From the convergent end 26, the legs 20 define a smooth and uniform taper along edges 28, each leg 20 ending in a rounded point 30.

The tick engaging slot 22 is sized such that it is of generally smaller dimensions than the body of a tick 12, thus permitting the removal thereof. The tick engaging slot 22 is generally V-shaped, and formed by edges 28 converging towards the convergent ends 26 of each leg, the convergence from edge 28 to edge 28 being gradually rounded rather than ending in a point, thereby forming rounded bend 34. Thus, when the tick engaging portion 18 is fitted around the neck of a tick 12, the likelihood of severing or excessively squeezing the tick 12 is reduced.

Furthermore, the rounded nature of the legs 20 allow smooth and easy entrapment of the tick 12 within the tick engaging slot 22. Accordingly, it is preferred that the surfaces of the tick engaging portion 18 be treated with appropriate smoothing and/or polishing processes. This will further reduce the likelihood of damage to the tick 12 prior to its removal from the host 14, while simultaneously reducing possible discomfort to the host 14. It should also be appreciated that the likelihood of cutting the host 14 is greatly reduced as is the possibility of being infected by organisms present on the body of the tick 12.

In a preferred embodiment of the invention, the tick removing device 10 is designed such that the tick engaging slot 22 has a maximum width of approximately 5/32 inch. A loop 36 is integrally formed from the end of the elongated body 16 opposite the tick engaging portion 18 in order to provide convenient storage and transportation. The tick removing device 10 may be constructed of various lightweight materials such as aluminum or plastic in order to decrease cost and weight.

In operation, the user must first locate the tick 12 which must be removed and accordingly push aside as much hair as possible from the area so that clear access to the tick 12 is provided. Next, the tick engaging slot 22 must be slipped around the neck portion of the tick 12. The actual removal of the tick 12 can be performed in several manners. First, the tick engaging slot 22 may be fitted around the neck of the tick 12 and the elongated handle 16 gently pulled until the snout of the tick 12 becomes unanchored from the skin of the host 14. Alternatively the tick engaging slot 22 may be fitted around the neck of the tick 12 and the elongated handle 16 pivoted about the pivotal surface 24 in order to gently and progressively dislodge the tick 12. Once removed, the tick 12 may be appropriately disposed or examined by a public health official.

It is to be understood that the present invention is not limited to the embodiment described above, but encompasses any and all embodiments within the scope of the following claims.

I claim:

1. A tick removing device comprising:

an elongated body; and, a tick engaging portion recurving towards said elongated body and integrally extending from said elongated body, said tick engaging portion comprising a substantially U-shaped curved portion having a pivotal surface for levering, said substantially U-shaped curved portion circumscribing an angle greater than 90° and conjoining said elongated body, said tick engaging portion further having a pair of legs each having a rounded point, each of said legs recurving in the same degree as the other, each of said legs positioned apart and configured to define a generally V-shaped tick engaging slot, each said leg having an edge converging from said rounded point to unitarily meet with an opposing edge at a rounded bend.

2. The tick removing device as recited in claim 1, wherein said tick engaging slot has a maximum width of 5/32 inch from said edge to said opposing edge.

3. The tick removing device as recited in claim 1, wherein said legs are processed to produce smooth surfaces thereon.

4. The tick removing device as recited in claim 1, further comprising a loop disposed at the end of said elongated body, said loop being integrally formed from said elongated body.

5. The tick removing device as recited in claim 4, wherein said elongated body, said legs, and said loop are constructed from aluminum.

6. The tick removing device as recited in claim 4, wherein said elongated body, said legs, and said loop are constructed from plastic.

\* \* \* \* \*